(12) United States Patent
Impellizzeri

(10) Patent No.: US 10,149,706 B2
(45) Date of Patent: Dec. 11, 2018

(54) DEVICE FOR COAPTATION OF BONE FRAGMENTS AND METHODS FOR PRODUCING SUCH A DEVICE

(71) Applicant: BIOTECH ORTHO, Salon de Provence (FR)

(72) Inventor: Frederic Impellizzeri, Salon de Provence (FR)

(73) Assignee: Biotech Ortho, Salon de Provence (FR)

( * ) Notice: Subject to any disclaimer, the term of this patent is extended or adjusted under 35 U.S.C. 154(b) by 772 days.

(21) Appl. No.: 14/421,021

(22) PCT Filed: Aug. 9, 2013

(86) PCT No.: PCT/FR2013/051920
§ 371 (c)(1),
(2) Date: Feb. 11, 2015

(87) PCT Pub. No.: WO2014/027160
PCT Pub. Date: Feb. 20, 2014

(65) Prior Publication Data
US 2015/0216571 A1 Aug. 6, 2015

(30) Foreign Application Priority Data
Aug. 13, 2012 (FR) ..................... 12 57787

(51) Int. Cl.
*A61B 17/80* (2006.01)
*A61B 17/00* (2006.01)

(52) U.S. Cl.
CPC ...... *A61B 17/8033* (2013.01); *A61B 17/8057* (2013.01); *A61B 17/8047* (2013.01); *A61B 2017/00526* (2013.01)

(58) Field of Classification Search
None
See application file for complete search history.

(56) References Cited

U.S. PATENT DOCUMENTS 5,013,313 A 5/1991 Surer
5,976,141 A 11/1999 Haag et al.
(Continued)

FOREIGN PATENT DOCUMENTS

EP 0 171 884 A1 2/1986
EP 0 345 133 A1 12/1989
(Continued)

OTHER PUBLICATIONS

International Search Report, dated Oct. 25, 2013, from corresponding PCT application.

*Primary Examiner* — Sameh Boles
(74) *Attorney, Agent, or Firm* — Duane Morris LLP

(57) ABSTRACT

A device for coaptation of bone parts or bone fragments, including an integral plate obtained by molding whereof one portion (1) is made from a first biocompatible polymer including at least one or, preferably, a plurality of areas or inserts (2) provided with a through hole (3), the areas or inserts being made from a second biocompatible polymer which is more malleable than the first polymer, the areas or inserts having mechanical properties allowing a self-tapping of the inner surface of the holes, via screws that can be used for securing the plate to bone tissue, the support portion and the areas or inserts having a partial molecular bond between them.

9 Claims, 2 Drawing Sheets

(56) References Cited

U.S. PATENT DOCUMENTS

| | | |
|---|---|---|
| 6,730,091 B1 | 3/2004 | Pfefferle et al. |
| 2006/0079900 A1 | 4/2006 | Mathieu et al. |
| 2010/0016858 A1* | 1/2010 | Michel ............... A61B 17/8057 606/70 |
| 2010/0234896 A1 | 9/2010 | Lorenz et al. |
| 2011/0022473 A1 | 9/2011 | Lewis et al. |
| 2012/0059376 A1 | 3/2012 | Rains et al. |
| 2012/0083846 A1 | 4/2012 | Wallenstein et al. |

FOREIGN PATENT DOCUMENTS

| | | |
|---|---|---|
| FR | 2 794 963 A1 | 12/2000 |
| JP | 6113963 | 1/1986 |
| JP | 2010500134 | 1/2010 |
| WO | 0066012 A1 | 11/2000 |
| WO | 2007010671 | 1/2007 |

* cited by examiner

DEVICE FOR COAPTATION OF BONE FRAGMENTS AND METHODS FOR PRODUCING SUCH A DEVICE

BACKGROUND OF THE INVENTION

Field of the Invention

The present invention concerns a device for coaptation of bone fragments. It also concerns methods of manufacturing such a device.

Description of the Related Art

The coaptation of bone fragments by means of plates of titanium or other material and screws, to perform osteosynthesis, is a common operation in bone surgery, for example in orthopedic surgery.

To achieve a good result, continuous clamping of the plates or implants on the bone fragments assembled by said implants is necessary. It is thus indispensable for the screws not to be able to unscrew and retract, to prevent any displacement of the implants relative to the bone fragments.

Furthermore, it would often be desirable to be able to choose the orientation of the screws relative to the plates, not only according to the positioning and form of the bone fragments to be assembled, but also in order to improve the quality of the assembly.

Lastly, it is of the utmost importance that application of the osteosynthesis or osteotomy plate to the bone be made with local bearing and not with bearing over the surface, in order to preserve the periosteum. More particularly, this vascularized membrane which covers the bone over its entire surface (with the exception of the articular cartilage), contains blood vessels which bring nutrients that are indispensable for the repair of the bone. Bones lacking a periosteum are thus incapable of regenerating and may suffer necrosis, and this is what occurs with an implant with bearing over the surface.

To counter the unscrewing and retraction of the screws, it has been proposed (EP-0.345.133, FR-2.794.963) to accommodate locking devices at the entrance to the holes provided in the plates for passage of the screws, in order to eliminate any possibility of axial retraction movement of said screws, after their screwing into the bone material. For example, it is provided in document EP-0.345.133, to use externally threaded counter-screws cooperating with complementary screw threading provided at the entrance to the holes for passing screws which the plates are provided with, such that the head of said screws is situated locked against a counter-screw and such that these latter cannot move axially relative to said plates, this fixing thereby ensuring the continuation of the bearing of the plate on the bone fragments.

These devices offered by a few manufacturers, today represent the most secure solutions in terms of locking. However, these relatively complex devices require the use of plates of relatively large thickness which is totally incompatible with use for operations on bones of the hand or bones of the foot without skin thickness, for which the thickness of the plates must be as small as possible, given the small size of the bones concerned and the small thickness of the skin.

SUMMARY OF THE INVENTION

In document EP-0.345.133, there is also shown a device for fastening together two members such as an implant and a bone, depending on whether the implant comprises holes for passing screws of which the axes are obliquely oriented relative to each other, such that the screws passing through those holes have orientations strictly imposed by the direction of said axes. Such a device can only be envisioned for the reduction of identical fractures, since it would otherwise be necessary to have as many models of plates as possible cases of fractures, which would be practically impossible; it does not in fact provide any possibility to choose the orientation of the screws according to the problems encountered in orthopedic surgery.

In document WO-00/66012 a plate for osteosynthesis is described which can be locked, depending on whether the screws and the holes for passing screws provided in the plate are respectively provided with screw threading for locking and with a meshing profile that are supposed to enable the insertion of the screws in the plate, in an inclined manner. The practical production of such a device would appear difficult and its efficacy has not been established, it would seem.

In general terms, in the field of the osteosynthesis of small bone fragments requiring the use of plates of small sizes, the devices currently present on the market do not enable angular play between the screws and the plate nor any immobilization, such that the screws are necessarily positioned perpendicularly to the plate. However, in certain cases, it would be desirable to be able to incline or orientate one or more screws, to use one or more bones of better quality for the screwing, or provide better possibilities of anchorage for said screws.

In document US-2011/0224737 a self-locking osteosynthesis device is described, comprising a plate provided with through holes formed from steel or titanium, the peripheries of those holes being constituted by inserts provided with an axial passage and made from a biocompatible material having mechanical properties enabling self-tapping of the inside wall delimiting the axial passage of said inserts by means of tapping screws which may be used for the fastening of said plate to bone parts or bone fragments, said inserts being made from thermoplastic polymer, for example polyetheretherketone (PEEK) and integrated into the metal plate by overmolding or mechanical assembly.

The drawback of the assembly by a method of overmolding is that the adherence between the surfaces of the metal plate and of the inserts of plastics material that are in contact is minimal due to the non-compatibility of these materials, such that the chemical anchorage between the metal plate and the plastic inserts is imperfect and such that said inserts may move while no longer providing the correct positioning of the immobilizing screws. The methods of mechanical assembly present the same drawback with in addition the difficulty of applying methods of automated mechanical assembly, in particular when the plate is not flat or has complex shapes.

The invention is in particular directed to mitigating the above-mentioned drawbacks of the osteosynthesis using plates and screws, in particular on account of the fact that the existing devices for major orthopedics (treatment of large traumas), cannot be transposed to the surgery of the hands and of the feet for which the size of the plates which may be used gets considerably smaller.

According to the invention, this object is attained by virtue of a device for coaptation of bone parts or bone fragments, comprising a one-piece molded plate of which a support portion is produced from a first biocompatible polymer and comprising at least one or preferably several zones or inserts provided with a through hole, said zones or inserts being produced from a second biocompatible polymer which is more malleable that the first polymer, said zones or inserts having mechanical properties enabling self-tapping of the inside surface of the holes, by means of screws usable for fastening said plate to bone tissues, that support portion and those zones or inserts presenting partial molecular melting together.

It substantially amounts to the same thing to state that the invention concerns a coaptation plate adapted to be fastened to bone fragments or that it is a device for coaptation of bone parts or bone fragments, or for instance that it is a osteosynthesis plate.

Thus the invention employs two polymer materials having a compatibility such that, by molding (simultaneous molding or overmolding), interdiffusion or interfusion occurs such that there is rheological continuity between the support portion and the zones or inserts. It should be understood that in this way, the aforesaid inserts are no longer clearly identifiable as in the known solutions. This results in mechanical strength properties of very good quality preventing any relative movement between the support portion and the zones and inserts, even having initially given a simple geometry to those zones and inserts (they may thus simply be cylindrical). Nevertheless the role of support portion is efficiently provided by the fact that the polymer material which constitutes it is a more rigid material than the material of the zones or inserts.

The aforementioned compatibility between the materials constituting the support portion and the zones or inserts may be defined in terms of rheology, and/or shrinkage, and/or adhesion and/or thermal properties; in fact, these various concepts express in different manner the capacity to interpenetrate by molding.

Another way to characterize the difference between the support portion and the zones or inserts is to state that the support portion is harder than the zones or inserts.

According to an embodiment, the first polymer from which is made the support portion of the coaptation plate (thus outside the zones or inserts constituted by the second polymer of lower rigidity), comprises a filler of implantable Carbon fibers.

Advantageously, that first polymer may comprise a hardening filler (for example the aforesaid carbon fibers) in a matrix formed by the second polymer; this promotes said aforementioned rheological continuity.

Thus, according to an advantageous provision of the invention, the zones or inserts of lower hardness are made from Polyetheretherketone (PEEK) and the polymer from which is made the support portion of the coaptation plate, outside the zones or inserts of lower hardness, is made from Polyetheretherketone (PEEK) with a filler of implantable Carbon fibers.

The invention has in particular as advantages:
to procure maximum adhesion thereby ensuring optimum cohesion of the connection between the zones or inserts of lower hardness and the support portion of the plate;
to give full latitude to the designer and producer of those devices regarding the geometry of the support portions, which may thus have a shape that as best possible approaches the zone at which coaptation is desired (one result may be appreciable comfort for the patient relative to the known solutions in which the inserts are carried by a metal plate, which is generally available only in simple shapes, flat or curved, but generally not having several curvatures in different planes—in particular in relation to surfaces referred to as "warped");
to eliminate or minimize the manual or mechanical operations of positioning inserts in an osteosynthesis or osteotomy plate, thereby enabling an increase in productivity.

Thanks to the above features, the self-tapping head of the screws produces its own helical receiving groove in the periphery of the holes in which they are engaged, such that said screws are then to be found automatically locked in the plate when their head is in tightened condition in its accommodation.

Furthermore, the osteosynthesis plate according to the invention enables selective angling of the screws relative to the axis of the holes of said plate, according to needs.

According to another advantageous provision, the plate has locally increased thicknesses on its underside (or side adapted to be placed facing the bone fragments of which it is desired to perform the coaptation) at the location of the zones or inserts of lower hardness.

For the manufacture of a coaptation device of the aforementioned type, the invention provides a method comprising forming in a mold at least one insert from a malleable biocompatible polymer material and injecting around that malleable biocompatible polymer material another biocompatible polymer material adapted to form a support portion of a plate of the coaptation device, under conditions of pressure, hardness and temperature such that rheological continuity occurs between the polymer materials resulting in a partial melting together of the materials so as to obtain a one-piece device.

For this it suffices to choose biocompatible polymer materials capable of melting together, and of interpenetrating with each other at the time of their cooling.

Advantageously, the two polymer materials differ only in the fact that one of the polymer materials contains a hardening filler, for example formed by carbon fibers.

According to a first example embodiment, the coaptation device according to the invention is produced by an overmolding method (the insert is produced in a first phase and the more rigid material is molded in a second phase).

According to another embodiment, the coaptation device according to the invention is produced by a bi-material injection molding method (this amounts to stating that the insert (or the inserts when there are several of them) and the support portion are produced simultaneously).

Thus the coaptation devices of the invention may be obtained by overmolding, or by bi-material injection molding.

Techniques enabling parts with inserts to be obtained have been known for several years.

Overmolding consists of putting in place, in the cavity of a hollow of an injection mold, a part A (or insert) and of injecting a material B. The filling of the cavity enables the overmolding to be carried out of part A with material B (definition taken from "Techniques de l'ingénieur©", which may be translated as "Techniques of the Engineer©")

The multi-material injection makes it possible to inject several polymers successively or simultaneously to produce a complex part. The first injected module consists of the insert, the following ones of the overmoldings (definition taken from the "Techniques de l'ingénieur©").

However, the concepts of overmolding or of multi-material injection do not per se imply that there is rheological continuity between the two materials, in contrast to what the invention provides.

The materials are advantageously chosen such that the material constituting the support portion has a melting point greater than that of the material constituting the inserts, such that, on molding the support portion, there is melting (in practice solely superficial) of the inserts so as to enable the rheological continuity to be obtained (the time of injection and of cooling being chosen such that the inserts are not kept too long at the melting point of the other material).

Cases that are particularly advantageous consist in using the material which is the most malleable as matrix of the more rigid material, that matrix containing a hardening filler, such as carbon, preferably in the form of fibers.

According to a first example of implementation, a coaptation device of the aforementioned type is obtained by an overmolding method comprising:

placing in a mold, at least one preformed part or insert made from a malleable biocompatible polymer;

injecting, into that mold, around said preformed part, a material formed from the same biocompatible polymer but with a Carbon filler, and having, after polymerization/molding, a higher rigidity than that of said preformed part or insert;

leaving the part to cool before ejecting it.

According to an advantageous feature, the malleable biocompatible material constituting the insert is Polyetheretherketone (natural PEEK).

According to another advantageous feature, the biocompatible material injected around the insert to constitute the support plate is PEEK with a filler of implantable Carbon fibers.

According to a desirable feature of the method of the invention, the injection is made into a mold of which the temperature is comprised between 140° C. and 220° C.

According to an example of implementation, the temperature of the mold is 175° C.

According to another desirable feature of the method of the invention, the biocompatible polymer with a carbon fiber filler is injected at a temperature comprised between 350° C. and 440° C.

According to an example embodiment, the biocompatible polymer with a Carbon fiber filler is injected at a temperature of 395° C.

According to another desirable feature of the method of the invention, the biocompatible polymer with a Carbon fiber filler is injected at a speed comprised between 50 g/sec and 750 g/sec.

According to an example embodiment, the biocompatible polymer with a Carbon fiber filler is injected at a speed of 300 g/sec.

According to another desirable feature of the method of the invention, the biocompatible polymer with a Carbon fiber filler is injected at a pressure comprised between 500 and 2000 Bars.

According to an example embodiment, the biocompatible polymer with a Carbon fiber filler is injected at a pressure of 1000 Bars.

According to still another desirable feature of the method, the device obtained requires a cooling time comprised between 10 seconds and 30 seconds.

According to an example of implementation, the cooling time of the device obtained is 20 seconds.

According to a second example of implementation, the coaptation device according to the invention is produced by a bi-material injection method comprising:

injecting into a mold, provided with two injection points to supply each of the materials, a malleable biocompatible polymer to manufacture said inserts and a polymer material formed from the same biocompatible polymer but with a Carbon fiber filler to manufacture the support portion, having after polymerization/molding a higher rigidity than that of the insert;

leaving the part, i.e. the device, to cool before ejecting it.

According to an advantageous feature, the malleable biocompatible material constituting the insert is Polyetheretherketone (natural PEEK).

According to another advantageous feature, the biocompatible material injected around the insert to constitute the support plate is PEEK with a filler of implantable Carbon fibers.

According to a desirable feature of the method of the invention, the injection is made into a mold of which the temperature is comprised between 140° C. and 220° C.

According to an example of implementation, the temperature of the mold is 175° C.

According to another desirable feature of the method of the invention, the biocompatible polymer with a Carbon fiber filler is injected at a temperature comprised between 350° C. and 440° C.

According to an example embodiment, the biocompatible polymer with a Carbon fiber filler is injected at a temperature of 395° C.

According to another desirable feature of the method of the invention, the biocompatible polymer with a Carbon fiber filler is injected at a speed comprised between 50 g/sec and 750 g/sec.

According to an example embodiment, the biocompatible polymer with a Carbon fiber filler is injected at a speed of 300 g/sec.

According to another desirable feature of the method of the invention, the biocompatible polymer with a Carbon fiber filler is injected at a pressure comprised between 500 and 2000 Bars.

According to an example embodiment, the biocompatible polymer with a Carbon fiber filler is injected at a pressure of 1000 Bars.

According to still another desirable feature of the method, the device obtained requires a cooling time comprised between 10 seconds and 30 seconds.

According to an example of implementation, the cooling time of the device obtained is 20 seconds.

The device and the methods according to the invention procure several desirable advantages. In particular:

to provide simpler, faster and cheaper manufacture of complex devices constituted by the two materials in question;

to enable skeletal rigidity to be reestablished thanks to the plate made from PEEK with a Carbon fiber filler and capable of bearing high loads while enabling the immobilization of the screw heads by compression of the malleable material in the screw threading of said screw heads thanks to the inserts of natural PEEK;

to procure the immobilization of the fastening screws of the osteosynthesis plates even if of small size, with angles of +/−10° and optimal compression;

to add locally increased thicknesses of the plate at the location of the PEEK inserts which, when it is placed on a bone, enable preservation of the periosteum of the bone required for proper reconstruction of the bone.

Furthermore, the coaptation device according to the invention entirely made from PEEK procures numerous advantages relative to the metal plates, i.e.

avoid the bony asperities which appear with metal plates and which are problematic on removal of the coaptation plate.

the possibility of having inserts injected by overmolding which is difficult to carry out on a metal plate, the folding step having poor repeatability. More particularly, acceptable results could be obtained with the overmolding method using very precise dimensions so as to avoid flash which the creep of the material gives rise to, which would make the manufacturing process too complex and too costly.

The coaptation device according to the invention and its methods of manufacture thus fully meet expectations, in particular those of surgeons, in terms of ease of manufacture, ease of putting in place and reliability in use.

The above objects, features and advantages, and still others, will be better apparent from the detailed description which follows and from the accompanying drawings in which:

BRIEF DESCRIPTION OF THE DRAWING FIGURES

DETAILED DESCRIPTION OF THE INVENTION

Figure 1:
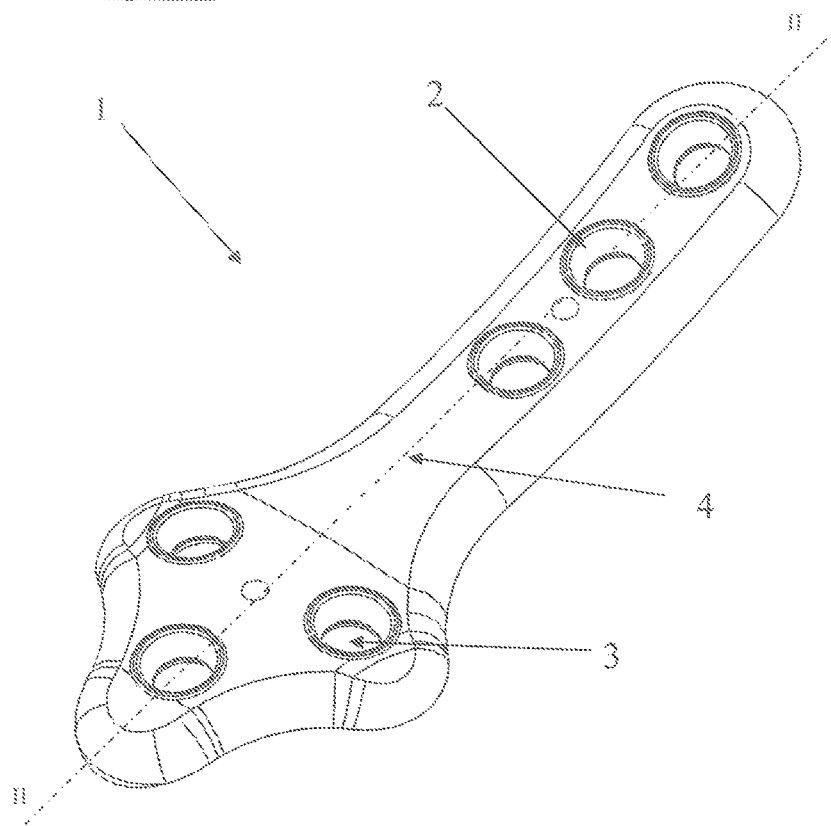
FIG. 1 is a perspective view of a first example embodiment of a osteosynthesis plate according to the invention, for use at the location of the medial malleolus.
Figure 2:
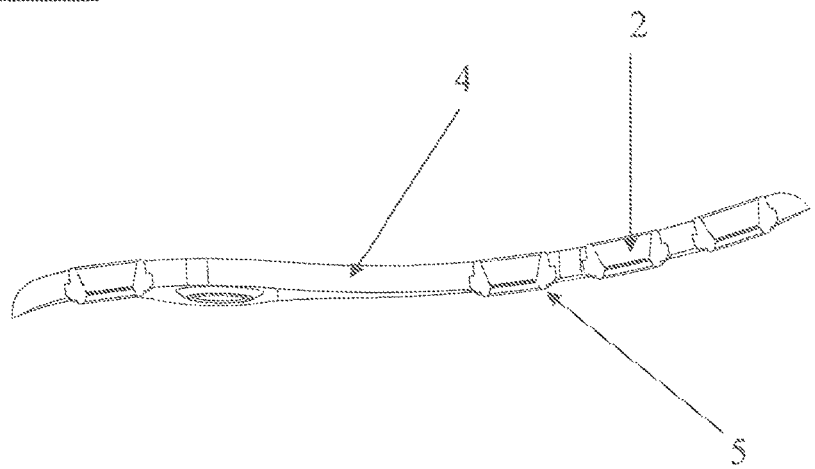
FIG. 2 is a cross-section view on line II-II of FIG. 1.
Figure 3:
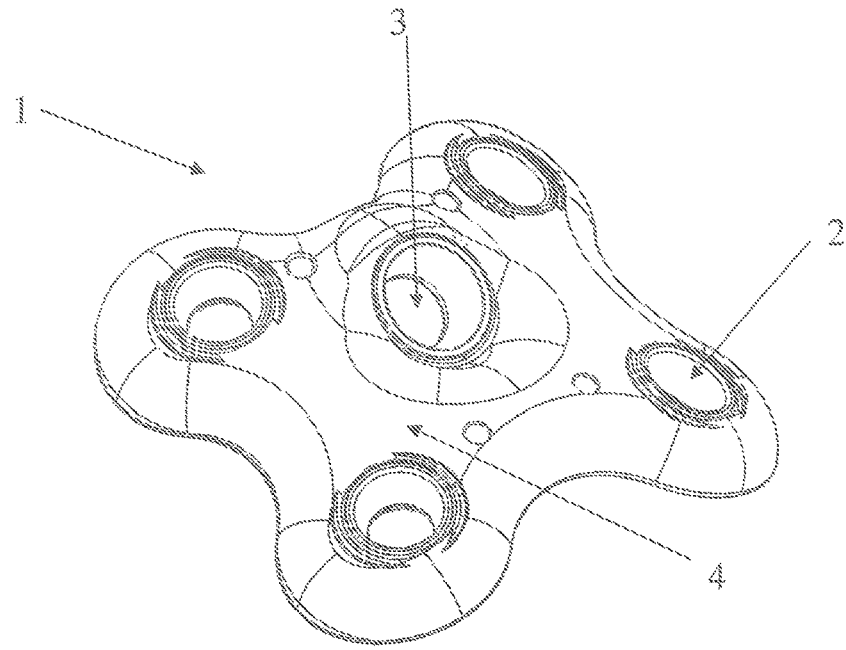
FIG. 3 is a perspective view of another, more complex example of an osteosynthesis plate according to the invention, for use at the location of the talonavicular joint.

Reference will be made to said drawings to describe an advantageous though non-limitative embodiment of the coaptation plate according to the invention and of implementation of methods of overmolding and of bi-material injection.

In the present disclosure and in the claims, the expression "underside" designates the face adapted to be placed facing the bone fragments of which the coaptation is desired to be carried out.

In the drawings, interfaces can be seen between the zones or inserts and their support portion; it should be clearly understood that these interfaces are only shown to enable the understanding of those drawings, whereas, since partial molecular melting together of one material with the other occurs, those interfaces are in fact not clearly constituted.

Coaptation Device

The coaptation device according to the invention is of an appropriate shape for the use which it is intended for. It is provided to be fastened to bone fragments, by means of screws (not shown) to ensure their coaptation. It comprises a plate 1 comprising a portion, referred to as support portion 4, is provided with at least one zone or insert 2 having a hole 3 made from a malleable biocompatible polymer presenting mechanical properties enabling self-tapping of the periphery of said holes by means of threaded screws usable for fastening said device, the remaining portion or support portion 4 of said plate 1 for coaptation of bone fragments being made from a biocompatible polymer with a Carbon filler and having, after polymerization/molding, a higher rigidity than that of the zone or insert or zones or inserts.

Advantageously, the plate comprises several inserts 2.

According to an advantageous feature, the zones or inserts 2 are made from natural Polyetheretherketone and the support portion 4 is made from PEEK with a with a filler of implantable Carbon fibers.

Figure 4:
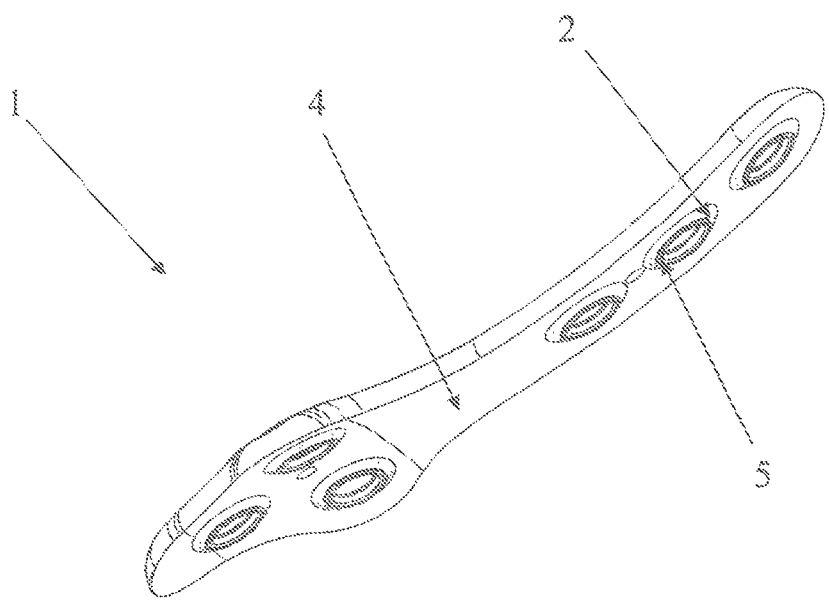
FIG. 4 is a detailed view of the osteosynthesis device according to the invention.

Advantageously and as illustrated in FIG. 4, the coaptation plate 1 has locally increased thicknesses 5 on the underside at the location of the inserts 2. More particularly, the inserts 2 enable those locally increased thicknesses 5 to be produced such that said plate is placed on bone fragments of which it is desired to perform the coaptation, the periosteum of said bone fragments is conserved, which enables better bone reconstruction.

According to a first example embodiment, the coaptation device 1 according to the invention is produced by a method of overmolding described below.

According to another embodiment, the coaptation device according to the invention is produced by a method of bi-material injection described below.

The Overmoldinq Method

Such a coaptation device including one or more of the aforementioned features, is obtained by an overmolding method comprising:

placing in a mold, at least one preformed part or insert made from a malleable biocompatible polymer;

injecting into that mold, around said preformed part, a biocompatible polymer with a filler of Carbon fibers, and having, after polymerization/molding, a higher rigidity than that of said preformed part or insert;

leaving the part to cool before ejecting it.

According to an advantageous feature, the malleable biocompatible material constituting the insert is Polyetheretherketone (natural PEEK).

According to another advantageous feature, the biocompatible material injected around the insert to constitute the support portion 4 of the plate 1 is PEEK with a filler of implantable Carbon fibers.

As the insert of natural PEEK and the PEEK with a Carbon fiber filler constituting the remainder of the plate are compatible, there is a chemical bond between the two materials and partial melting together optimizing the strength of that bond.

As the strength of that bond may be affected by different factors, such as the temperature at the interface, the cleanliness of the insert or the melting point, or the geometry of the interface, it is necessary to comply with certain conditions.

Thus, according to the method of the invention, the injection is made in a mold of which the temperature is comprised between 140° C. and 220° C., and more particularly at a temperature of 175° C.

According to another feature of the method of the invention, the biocompatible polymer with a Carbon filler is injected at a temperature comprised between 350° C. and 440° C. Advantageously, it is injected at a temperature of 395° C.

The biocompatible polymer with a Carbon filler is injected at a speed comprised between 50 g/sec and 750 g/sec. For example, it is injected at a speed of 300 g/sec.

According to the method of the invention, it is preferable to avoid extremely high holding pressures. Thus, the biocompatible polymer with a Carbon filler is injected at a pressure comprised between 500 and 2000 Bars. Advantageously, it is injected at a pressure of 1000 Bars.

In order to avoid excessive shrinkage (that is to say the retraction of the material at the time of its cooling at the end of overmolding) at the final phase of production and thus avoid a possibility of functional loss, the device obtained requires a cooling time comprised between 10 seconds and 30 seconds. Preferably, the cooling time of the device obtained is 20 seconds.

The Bi-Injection Method

According to another example of implementation, a coaptation device according to the invention is obtained by a bi-material injection method comprising:

injecting into a mold, provided with two injection points to supply each of the materials, a biocompatible polymer (PEEK) to manufacture said inserts and a biocompatible polymer with a Carbon fiber filler to manufacture the support portion 4 of the plate 1, having after polymerization/molding a higher rigidity than that of the insert;

leaving the part to cool before ejecting it.

According to an advantageous feature, the malleable biocompatible material constituting the insert is Polyetheretherketone (PEEK).

According to another advantageous feature, the biocompatible material injected around the insert to constitute the support portion 4 of the plate 1 is PEEK with a filler of implantable Carbon fibers.

As the insert of PEEK and the PEEK with a Carbon filler constituting the remaining part of the plate, i.e. the support portion, are compatible, there is a chemical bond between the two materials and partial melting together optimizing the strength of that bond.

As the strength of that bond may be affected by different factors, such as the temperature at the interface, the cleanliness of the insert or the melting point, it is necessary to comply with certain conditions.

Thus, according to the method of the invention, the injection is made in a mold of which the temperature is comprised between 140° C. and 220° C., and more particularly at a temperature of 175° C.

According to another feature of the method of the invention, the biocompatible polymer with a Carbon filler is injected at a temperature comprised between 350° C. and 440° C. Advantageously, it is injected at a temperature of 395° C.

The biocompatible polymer with a Carbon filler is injected at a speed comprised between 50 g/sec and 750 g/sec. For example, it is injected at a speed of 300 g/sec.

According to the method of the invention, it is imperative to avoid extremely high holding pressures. Thus, the biocompatible polymer with a Carbon filler is injected at a pressure comprised between 500 and 2000 Bars. Advantageously, it is injected at a pressure of 1000 Bars.

In order to avoid excessive shrinkage (that is to say the retraction of the material at the time of its cooling at the end of injection) at the final phase of production and thus avoid a possibility of functional loss, the device obtained requires a cooling time comprised between 10 seconds and 30 seconds. Preferably, the cooling time of the device obtained is 20 seconds.

The invention claimed is:

1. A device for coaptation of bone parts or bone fragments, comprising:
    a one-piece molded plate comprising a support portion produced from a first biocompatible polymer and comprising at least one zone or insert which is provided with a through hole and which is produced from a second biocompatible polymer which is more malleable than the first polymer, said at least one zone or insert having mechanical properties enabling self-tapping of the inside surface of the through hole, by means of screws adapted for fastening said plate to bone tissues,
    wherein the support portion and the at least one zone or insert present partial molecular melting together.

2. The device for coaptation of bone parts or bone fragments according to claim 1, wherein the first biocompatible polymer from which is made the support portion, outside the at least one zone or insert constituted by the second biocompatible polymer of lower rigidity, comprises a filler of implantable carbon fibers.

3. The device for coaptation of bone parts or bone fragments according to claim 1, wherein the first biocompatible polymer comprises a hardening filler in a matrix formed by the second biocompatible polymer.

4. The device for coaptation of bone parts or bone fragments according to claim 1, wherein the at least one zone or insert are made from polyetheretherketone (PEEK) and the first biocompatible polymer from which is made the support portion, outside the at least one zone or insert, is made from polyetheretherketone (PEEK) with a filler of implantable carbon fibers.

5. The device for coaptation of bone parts or bone fragments according to claim 1, wherein the plate has locally increased thicknesses on the underside at the location of the at least one zone or insert.

6. The device for coaptation of bone parts or bone fragments according to claim 1, wherein the plate is produced by an overmolding method.

7. The device for coaptation of bone parts or bone fragments according to claim 1, wherein the plate is produced by a bi-material injection method.

8. The device for coaptation of bone parts or bone fragments according to claim 1, wherein several zones or inserts are provided.

9. The device for coaptation of bone parts or bone fragments according to claim 1, wherein the second biocompatible polymer has a melting point that is lower than that of the first biocompatible polymer, and wherein the support portion and the at least one zone or insert have a rheological continuity therebetween resulting in their partial molecular melting that is achieved through a solely superficial melting of the at least one zone or insert upon molding of the support portion.

* * * * *

UNITED STATES PATENT AND TRADEMARK OFFICE
CERTIFICATE OF CORRECTION

PATENT NO. : 10,149,706 B2  
APPLICATION NO. : 14/421021  
DATED : December 11, 2018  
INVENTOR(S) : Frederic Impellizzeri Page 1 of 1

It is certified that error appears in the above-identified patent and that said Letters Patent is hereby corrected as shown below:

On the Title Page

Item [73], delete:
"Biotech Ortho, Salon de Provence (FR)"
Insert:
--Tornier, Montbonnot-Saint-Martin (FR)--

Signed and Sealed this
Second Day of June, 2020

Andrei Iancu
*Director of the United States Patent and Trademark Office*